United States Patent
Bruewer et al.

(10) Patent No.: US 9,125,649 B2
(45) Date of Patent: Sep. 8, 2015

(54) SURGICAL INSTRUMENT WITH FILLED STAPLE

(75) Inventors: Dean B. Bruewer, Fairfield, OH (US); Cory G. Kimball, Cincinnati, OH (US); William A. Daunch, Cary, NC (US); Brett E. Swensgard, West Chester, OH (US); Katherine J. Schmid, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 264 days.

(21) Appl. No.: 13/233,646

(22) Filed: Sep. 15, 2011

(65) Prior Publication Data

US 2013/0068815 A1    Mar. 21, 2013

(51) Int. Cl.
  *A61B 17/068*  (2006.01)
  *A61B 17/064*  (2006.01)
  *A61B 17/072*  (2006.01)
  *A61B 17/00*   (2006.01)

(52) U.S. Cl.
  CPC ....... *A61B 17/0644* (2013.01); *A61B 17/07207* (2013.01); *A61B 17/00491* (2013.01); *A61B 2017/00004* (2013.01); *A61B 2017/00495* (2013.01); *A61B 2017/00893* (2013.01); *A61B 2017/00951* (2013.01)

(58) Field of Classification Search
  CPC ............... A61B 17/07207; A61B 2017/07214; A61B 17/072
  USPC ............... 227/19, 175.1, 176.1, 178.1, 180.1, 227/181.1; 206/336; 606/153, 219
  See application file for complete search history.

(56) References Cited

U.S. PATENT DOCUMENTS

| | | |
|---|---|---|
| 2,303,131 A | 11/1942 | Morgan |
| 3,364,200 A | 1/1968 | Ashton et al. |
| 3,496,940 A | 2/1970 | Steinman |
| 3,526,228 A | 9/1970 | Lyng |
| 4,222,383 A | 9/1980 | Schossow |
| 4,513,746 A | 4/1985 | Aranyi et al. |
| 4,549,545 A | 10/1985 | Levy |
| 4,610,250 A | 9/1986 | Green |
| 4,693,720 A | 9/1987 | Scharnberg et al. |

(Continued)

FOREIGN PATENT DOCUMENTS

| | | |
|---|---|---|
| CA | 481943 | 2/1947 |
| EP | 328 401 | 8/1989 |

(Continued)

OTHER PUBLICATIONS

Abstract for FR2789885.

(Continued)

*Primary Examiner* — Nathaniel Chukwurah
(74) *Attorney, Agent, or Firm* — Frost Brown Todd LLC

(57) ABSTRACT

An apparatus comprises a surgical instrument having a proximal end and a distal end. The proximal end may comprise a handle. The distal end may comprise a cutter and a stapler. The apparatus may further comprise a staple for use with the stapler. The staple may comprise an inner channel extending along at least a portion of the length of the staple. The apparatus may further comprise an agent contained in the inner channel, which may be used to coagulate a surgical site where surgical instrument is used. The agent may facilitate coagulation of the fluids at a surgical site once the staples are anchored to the surgical site.

20 Claims, 10 Drawing Sheets

(56) References Cited

U.S. PATENT DOCUMENTS

| | | |
|---|---|---|
| 4,805,823 A | 2/1989 | Rothfuss |
| 4,976,722 A | 12/1990 | Failla |
| 5,011,493 A | 4/1991 | Belykh et al. |
| 5,064,057 A | 11/1991 | Iwatsuki et al. |
| 5,171,249 A | 12/1992 | Stefanchik et al. |
| 5,263,629 A | 11/1993 | Trumbull et al. |
| 5,282,829 A * | 2/1994 | Hermes .................. 606/219 |
| 5,297,324 A | 3/1994 | Su |
| 5,327,914 A | 7/1994 | Shlain |
| 5,366,480 A | 11/1994 | Corriveau et al. |
| 5,383,904 A | 1/1995 | Totakura et al. |
| 5,393,594 A | 2/1995 | Koyfman et al. |
| 5,409,498 A | 4/1995 | Braddock et al. |
| 5,411,193 A | 5/1995 | Culp |
| 5,415,334 A | 5/1995 | Williamson, IV et al. |
| 5,465,895 A | 11/1995 | Knodel et al. |
| 5,466,462 A | 11/1995 | Rosenthal et al. |
| 5,496,603 A | 3/1996 | Riedel et al. |
| 5,503,638 A | 4/1996 | Cooper et al. |
| 5,542,594 A | 8/1996 | McKean et al. |
| 5,565,210 A | 10/1996 | Rosenthal et al. |
| 5,597,107 A | 1/1997 | Knodel et al. |
| 5,607,590 A | 3/1997 | Simizu |
| 5,607,686 A | 3/1997 | Totakura et al. |
| 5,626,587 A | 5/1997 | Bishop et al. |
| 5,632,432 A | 5/1997 | Schulze et al. |
| 5,639,851 A | 6/1997 | Bezwada et al. |
| 5,641,566 A | 6/1997 | Kranzler et al. |
| 5,644,002 A | 7/1997 | Cooper et al. |
| 5,673,840 A | 10/1997 | Schulze et al. |
| 5,690,675 A | 11/1997 | Sawyer et al. |
| 5,704,534 A | 1/1998 | Huitema et al. |
| 5,711,958 A | 1/1998 | Cohn et al. |
| 5,733,308 A | 3/1998 | Daugherty et al. |
| 5,749,968 A | 5/1998 | Melanson et al. |
| 5,752,965 A | 5/1998 | Francis et al. |
| 5,755,778 A | 5/1998 | Kleshinski |
| 5,766,188 A | 6/1998 | Igaki |
| 5,769,892 A | 6/1998 | Kingwell |
| 5,804,213 A * | 9/1998 | Rolf .................. 424/445 |
| 5,810,855 A | 9/1998 | Rayburn et al. |
| 5,814,055 A | 9/1998 | Knodel et al. |
| 5,814,057 A | 9/1998 | Oi et al. |
| 5,843,096 A | 12/1998 | Igaki et al. |
| 5,902,312 A | 5/1999 | Frater et al. |
| 5,921,956 A | 7/1999 | Grinberg et al. |
| 5,997,895 A | 12/1999 | Narotam et al. |
| 6,010,054 A | 1/2000 | Johnson et al. |
| 6,019,791 A | 2/2000 | Wood |
| 6,031,148 A | 2/2000 | Hayes et al. |
| 6,099,551 A | 8/2000 | Gabbay |
| 6,174,333 B1 | 1/2001 | Kadiyala et al. |
| 6,203,564 B1 | 3/2001 | Hutton et al. |
| 6,245,081 B1 | 6/2001 | Bowman et al. |
| 6,273,897 B1 | 8/2001 | Dalessandro et al. |
| 6,277,397 B1 | 8/2001 | Shimizu |
| 6,312,474 B1 | 11/2001 | Francis et al. |
| 6,325,810 B1 | 12/2001 | Hamilton et al. |
| 6,355,699 B1 | 3/2002 | Vyakarnam et al. |
| 6,488,197 B1 | 12/2002 | Whitman |
| 6,495,127 B1 | 12/2002 | Wallace et al. |
| 6,511,748 B1 | 1/2003 | Barrows |
| 6,592,597 B2 | 7/2003 | Grant et al. |
| 6,638,285 B2 | 10/2003 | Gabbay |
| 6,656,193 B2 | 12/2003 | Grant et al. |
| 6,704,210 B1 | 3/2004 | Myers |
| 6,814,741 B2 | 11/2004 | Bowman et al. |
| 6,835,336 B2 | 12/2004 | Watt |
| 6,921,412 B1 | 7/2005 | Black et al. |
| 6,962,594 B1 | 11/2005 | Thevenet |
| 6,978,921 B2 | 12/2005 | Shelton, IV et al. |
| 7,000,818 B2 | 2/2006 | Shelton, IV et al. |
| 7,048,755 B2 | 5/2006 | Bonutti et al. |
| 7,084,082 B1 | 8/2006 | Shimizu |
| 7,143,923 B2 | 12/2006 | Shelton, IV et al. |
| 7,147,138 B2 | 12/2006 | Shelton, IV |
| 7,207,471 B2 | 4/2007 | Heinrich et al. |
| 7,211,093 B2 | 5/2007 | Sauer et al. |
| 7,268,205 B2 | 9/2007 | Williams et al. |
| 7,303,108 B2 | 12/2007 | Shelton, IV |
| 7,335,212 B2 | 2/2008 | Edoga et al. |
| 7,367,485 B2 | 5/2008 | Shelton, IV et al. |
| 7,377,928 B2 | 5/2008 | Zubik et al. |
| 7,380,695 B2 | 6/2008 | Doll et al. |
| 7,380,696 B2 | 6/2008 | Shelton, IV et al. |
| 7,404,508 B2 | 7/2008 | Smith et al. |
| 7,434,715 B2 | 10/2008 | Shelton, IV et al. |
| 7,517,356 B2 | 4/2009 | Heinrich |
| 7,607,557 B2 | 10/2009 | Shelton, IV et al. |
| 7,721,930 B2 | 5/2010 | McKenna et al. |
| 7,738,971 B2 | 6/2010 | Swayze et al. |
| 7,842,025 B2 | 11/2010 | Coleman et al. |
| 7,845,533 B2 | 12/2010 | Marczyk et al. |
| 8,097,017 B2 | 1/2012 | Viola |
| 8,308,659 B2 | 11/2012 | Scheibe et al. |
| 8,403,945 B2 | 3/2013 | Whitfield et al. |
| 8,475,453 B2 | 7/2013 | Marczyk et al. |
| 2002/0165559 A1 | 11/2002 | Grant et al. |
| 2003/0120284 A1 | 6/2003 | Palacios et al. |
| 2003/0163085 A1 | 8/2003 | Tanner et al. |
| 2003/0183671 A1 | 10/2003 | Mooradian et al. |
| 2004/0093024 A1 | 5/2004 | Lousararian et al. |
| 2004/0167572 A1 * | 8/2004 | Roth et al. .................. 606/219 |
| 2004/0254608 A1 | 12/2004 | Huitema et al. |
| 2005/0042250 A1 | 2/2005 | Damien et al. |
| 2005/0059996 A1 | 3/2005 | Bauman et al. |
| 2005/0070929 A1 | 3/2005 | Dalessandro et al. |
| 2005/0101834 A1 | 5/2005 | Merade |
| 2005/0107810 A1 | 5/2005 | Morales et al. |
| 2005/0145671 A1 | 7/2005 | Viola |
| 2005/0154403 A1 | 7/2005 | Sauer et al. |
| 2005/0245965 A1 | 11/2005 | Orban, III et al. |
| 2005/0249772 A1 | 11/2005 | Malaviya et al. |
| 2005/0251153 A1 | 11/2005 | Sakamoto et al. |
| 2005/0283256 A1 | 12/2005 | Sommerich et al. |
| 2005/0288767 A1 | 12/2005 | Kujawski et al. |
| 2006/0004388 A1 | 1/2006 | Whayne et al. |
| 2006/0004407 A1 | 1/2006 | Hiles et al. |
| 2006/0047312 A1 | 3/2006 | Garcia Olmo et al. |
| 2006/0093655 A1 | 5/2006 | Bar et al. |
| 2006/0094318 A1 | 5/2006 | Matsuda et al. |
| 2006/0129225 A1 | 6/2006 | Kopia et al. |
| 2006/0135992 A1 | 6/2006 | Bettuchi et al. |
| 2006/0173470 A1 | 8/2006 | Oray et al. |
| 2006/0212069 A1 | 9/2006 | Shelton, IV |
| 2006/0229672 A1 | 10/2006 | Forsberg |
| 2006/0235469 A1 * | 10/2006 | Viola .................. 606/219 |
| 2006/0265006 A1 | 11/2006 | White et al. |
| 2006/0265007 A1 | 11/2006 | White et al. |
| 2007/0016227 A1 | 1/2007 | de la Torre et al. |
| 2007/0034667 A1 | 2/2007 | Holsten et al. |
| 2007/0034669 A1 | 2/2007 | de la Torre et al. |
| 2007/0049953 A2 | 3/2007 | Shimoji et al. |
| 2007/0060932 A1 | 3/2007 | Stack et al. |
| 2007/0066981 A1 | 3/2007 | Meagher |
| 2007/0112360 A1 | 5/2007 | De Deyne et al. |
| 2007/0128243 A1 | 6/2007 | Serafica et al. |
| 2007/0131732 A1 | 6/2007 | Holsten et al. |
| 2007/0150002 A1 | 6/2007 | Szabo et al. |
| 2007/0156140 A1 | 7/2007 | Baily |
| 2007/0190108 A1 | 8/2007 | Datta et al. |
| 2007/0207180 A1 | 9/2007 | Tanihara et al. |
| 2007/0213522 A1 | 9/2007 | Harris et al. |
| 2007/0219571 A1 | 9/2007 | Balbierz et al. |
| 2007/0225642 A1 | 9/2007 | Houser et al. |
| 2007/0243227 A1 | 10/2007 | Gertner |
| 2007/0246505 A1 | 10/2007 | Pace-Floridia et al. |
| 2007/0286892 A1 | 12/2007 | Herzberg et al. |
| 2008/0015598 A1 * | 1/2008 | Prommersberger .......... 606/75 |
| 2008/0039871 A1 | 2/2008 | Wallace et al. |
| 2008/0077131 A1 | 3/2008 | Yates et al. |
| 2008/0078800 A1 | 4/2008 | Hess et al. |
| 2008/0078801 A1 | 4/2008 | Shelton, IV et al. |
| 2008/0078802 A1 | 4/2008 | Hess et al. |

(56) References Cited

U.S. PATENT DOCUMENTS

| | | | |
|---|---|---|---|
| 2008/0078803 | A1 | 4/2008 | Shelton, IV et al. |
| 2008/0078804 | A1 | 4/2008 | Shelton, IV et al. |
| 2008/0078805 | A1 | 4/2008 | Omaits et al. |
| 2008/0078806 | A1 | 4/2008 | Omaits et al. |
| 2008/0078807 | A1 | 4/2008 | Hess et al. |
| 2008/0081881 | A1 | 4/2008 | Swetlin et al. |
| 2008/0082124 | A1 | 4/2008 | Hess et al. |
| 2008/0082126 | A1 | 4/2008 | Murray et al. |
| 2008/0110959 | A1 | 5/2008 | Orban, III et al. |
| 2008/0110961 | A1 | 5/2008 | Voegele et al. |
| 2008/0114381 | A1 | 5/2008 | Voegele et al. |
| 2008/0114385 | A1 | 5/2008 | Byrum et al. |
| 2008/0114399 | A1 | 5/2008 | Bonutti |
| 2008/0125812 | A1 | 5/2008 | Zubik et al. |
| 2008/0128469 | A1 | 6/2008 | Dalessandro et al. |
| 2008/0140115 | A1 | 6/2008 | Stopek |
| 2008/0200949 | A1 | 8/2008 | Hiles et al. |
| 2008/0314960 | A1 | 12/2008 | Marczyk et al. |
| 2009/0001122 | A1 | 1/2009 | Prommersberger et al. |
| 2009/0076510 | A1 | 3/2009 | Bell et al. |
| 2009/0082855 | A1* | 3/2009 | Borges et al. ............... 623/1.42 |
| 2009/0118747 | A1 | 5/2009 | Bettuchi et al. |
| 2010/0127041 | A1* | 5/2010 | Morgan et al. ............. 227/175.1 |
| 2010/0331880 | A1 | 12/2010 | Stopek |
| 2011/0172705 | A1* | 7/2011 | Hadba et al. .................. 606/219 |

FOREIGN PATENT DOCUMENTS

| | | |
|---|---|---|
| EP | 0531742 | 3/1993 |
| EP | 0 667 119 | 8/1995 |
| EP | 0 781 564 | 7/1997 |
| EP | 0 818 470 | 1/1998 |
| EP | 1 098 024 | 5/2001 |
| EP | 1 229 841 | 8/2002 |
| EP | 1 494 596 | 1/2005 |
| EP | 1 621 141 | 2/2006 |
| EP | 1 647 286 | 4/2006 |
| EP | 1 759 640 | 3/2007 |
| EP | 1 836 974 | 9/2007 |
| FR | 2706280 | 12/1994 |
| FR | 2 789 885 | 8/2000 |
| FR | 2 850 281 | 7/2004 |
| GB | 222 954 | 10/1924 |
| GB | 493 459 | 10/1938 |
| GB | 913 218 | 12/1962 |
| JP | 107 2740 | 3/1989 |
| JP | 3146773 | 6/1991 |
| JP | 5076586 | 3/1993 |
| JP | 11309151 | 11/1999 |
| WO | WO 93/10731 | 6/1993 |
| WO | WO 98/38923 | 9/1998 |
| WO | WO 01/17446 | 3/2001 |
| WO | WO 02/09593 | 2/2002 |
| WO | WO 02/22184 | 3/2002 |
| WO | WO 03/094743 | 11/2003 |
| WO | WO 2004/060425 | 7/2004 |
| WO | WO 2006/081174 | 8/2006 |
| WO | WO 2006/106269 | 10/2006 |
| WO | WO 2007/067621 | 6/2007 |
| WO | WO 2008/057281 | 5/2008 |
| WO | WO 2011/044343 | 4/2011 |

OTHER PUBLICATIONS

Abstract for FR2850281.
Abstract for JP1072740.
Abstract for JP11309151.
Abstract for JP3146773.
Abstract for JP5076586.
International Search Report dated Nov. 27, 2012 for Application No. PCT/US2012/054410.
International Search Report and Written Opinion dated Jan. 30, 2014 For Application No. PCT/US2013/060537.
International Search Report and Written Opinion dated Jan. 31, 2014 for Application No. PCT/US 2013/060536.

* cited by examiner

SURGICAL INSTRUMENT WITH FILLED STAPLE

BACKGROUND

In some settings, endoscopic surgical instruments may be preferred over traditional open surgical devices since a smaller incision may reduce the post-operative recovery time and complications. Consequently, some endoscopic surgical instruments may be suitable for placement of a distal end effector at a desired surgical site through a cannula of a trocar. These distal end effectors may engage tissue in a number of ways to achieve a diagnostic or therapeutic effect (e.g., endocutter, grasper, cutter, stapler, clip applier, access device, drug/gene therapy delivery device, and energy delivery device using ultrasound, RF, laser, etc.). Endoscopic surgical instruments may include a shaft between the end effector and a handle portion, which is manipulated by the clinician. Such a shaft may enable insertion to a desired depth and rotation about the longitudinal axis of the shaft, thereby facilitating positioning of the end effector within the patient. Positioning of an end effector may be further facilitated through inclusion of one or more articulation joints or features, enabling the end effector to be selectively articulated or otherwise deflected relative to the longitudinal axis of the shaft.

Examples of endoscopic surgical instruments include surgical staplers. Some such staplers are operable to clamp down on layers of tissue, cut through the clamped layers of tissue, and drive staples through the layers of tissue to substantially seal the severed layers of tissue together near the severed ends of the tissue layers. Merely exemplary surgical staplers are disclosed in U.S. Pat. No. 4,805,823, entitled "Pocket Configuration for Internal Organ Staplers," issued Feb. 21, 1989; U.S. Pat. No. 5,415,334, entitled "Surgical Stapler and Staple Cartridge," issued May 16, 1995; U.S. Pat. No. 5,465,895, entitled "Surgical Stapler Instrument," issued Nov. 14, 1995; U.S. Pat. No. 5,597,107, entitled "Surgical Stapler Instrument," issued Jan. 28, 1997; U.S. Pat. No. 5,632,432, entitled "Surgical Instrument," issued May 27, 1997; U.S. Pat. No. 5,673,840, entitled "Surgical Instrument," issued Oct. 7, 1997; U.S. Pat. No. 5,704,534, entitled "Articulation Assembly for Surgical Instruments," issued Jan. 6, 1998; U.S. Pat. No. 5,814,055, entitled "Surgical Clamping Mechanism," issued Sep. 29, 1998; U.S. Pat. No. 6,978,921, entitled "Surgical Stapling Instrument Incorporating an E-Beam Firing Mechanism," issued Dec. 27, 2005; U.S. Pat. No. 7,000,818, entitled "Surgical Stapling Instrument Having Separate Distinct Closing and Firing Systems," issued Feb. 21, 2006; U.S. Pat. No. 7,143,923, entitled "Surgical Stapling Instrument Having a Firing Lockout for an Unclosed Anvil," issued Dec. 5, 2006; U.S. Pat. No. 7,303,108, entitled "Surgical Stapling Instrument Incorporating a Multi-Stroke Firing Mechanism with a Flexible Rack," issued Dec. 4, 2007; U.S. Pat. No. 7,367,485, entitled "Surgical Stapling Instrument Incorporating a Multistroke Firing Mechanism Having a Rotary Transmission," issued May 6, 2008; U.S. Pat. No. 7,380,695, entitled "Surgical Stapling Instrument Having a Single Lockout Mechanism for Prevention of Firing," issued Jun. 3, 2008; U.S. Pat. No. 7,380,696, entitled "Articulating Surgical Stapling Instrument Incorporating a Two-Piece E-Beam Firing Mechanism," issued Jun. 3, 2008; U.S. Pat. No. 7,404,508, entitled "Surgical Stapling and Cutting Device," issued Jul. 29, 2008; U.S. Pat. No. 7,434,715, entitled "Surgical Stapling Instrument Having Multistroke Firing with Opening Lockout," issued Oct. 14, 2008; and U.S. Pat. No. 7,721,930, entitled "Disposable Cartridge with Adhesive for Use with a Stapling Device," issued May 25, 2010. The disclosure of each of the above-cited U.S. Patents is incorporated by reference herein. While the surgical staplers referred to above are described as being used in endoscopic procedures, it should be understood that such surgical staplers may also be used in open procedures and/or other non-endoscopic procedures.

While various kinds of surgical stapling instruments and associated components have been made and used, it is believed that no one prior to the inventor(s) has made or used the invention described in the appended claims.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

Figure 1A:
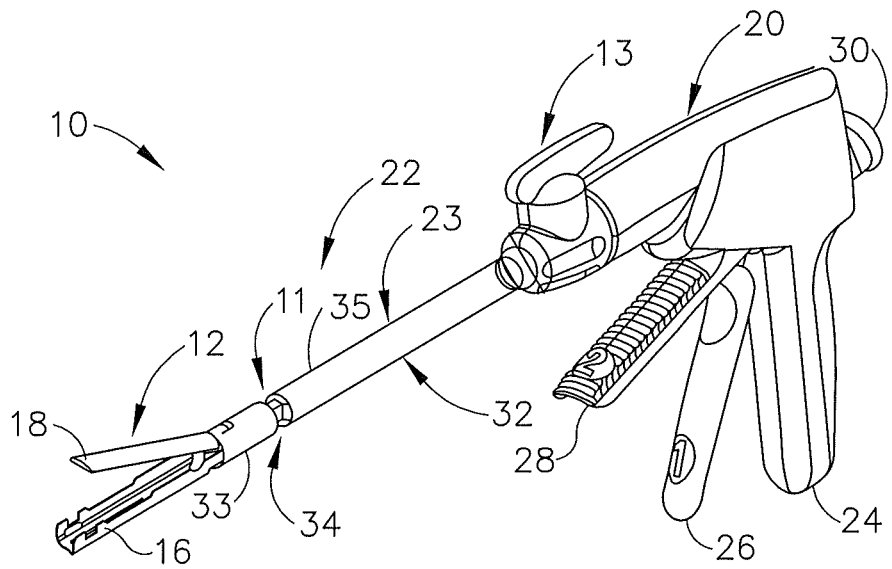
FIG. 1A depicts a perspective view of an articulating surgical instrument with an end effector in a nonarticulated position.
Figure 1B:
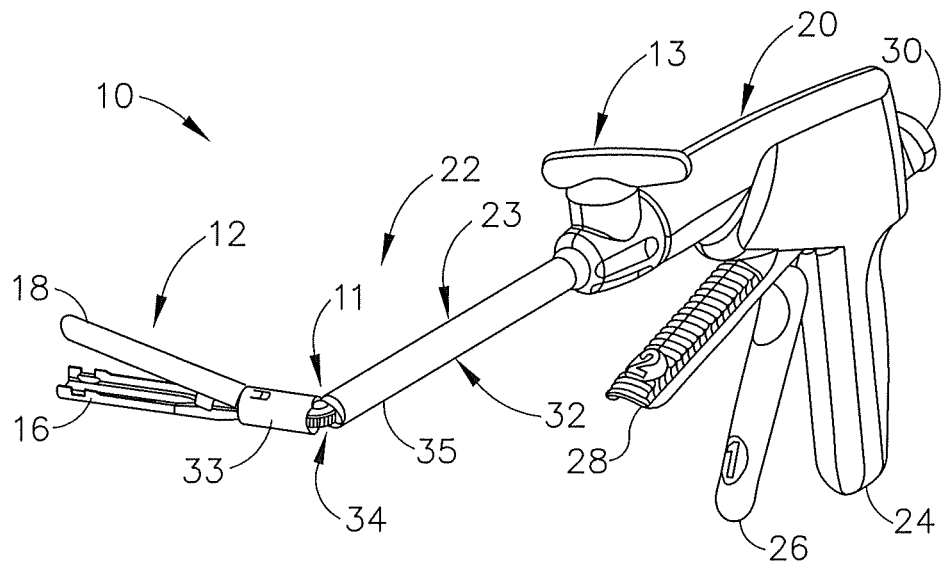
FIG. 1B depicts a perspective view of the surgical instrument of FIG. 1A with an end effector in an articulated position.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

I. Exemplary Surgical Stapler

FIGS. 1-6 depict an exemplary surgical stapling and severing instrument (10) that is sized for insertion, in a nonarticulated state as depicted in FIG. 1A, through a trocar cannula passageway to a surgical site in a patient for performing a surgical procedure. Surgical and stapling and severing instrument (10) includes handle portion (20) connected to implement portion (22), the latter further comprising shaft (23) distally terminating in an articulating mechanism (11) and a distally attached end effector (12). Once articulation mechanism (11) and distally end effector (12) are inserted through the cannula passageway of a trocar, articulation mechanism (11) may be remotely articulated, as depicted in FIG. 1B, by articulation control (13). Thereby, end effector (12) may reach behind an organ or approach tissue from a desired angle or for other reasons. It should be understood that terms such as "proximal" and "distal" are used herein with reference to a clinician gripping handle portion (20) of instrument (10). Thus, end effector (12) is distal with respect to the more proximal handle portion (20). It will be further appreciated that for convenience and clarity, spatial terms such as "vertical" and "horizontal" are used herein with respect to the drawings. However, surgical instruments are used in many orientations and positions, and these terms are not intended to be limiting and absolute.

End effector (12) of the present example includes a lower jaw (16) and a pivotable anvil (18). Handle portion (20) includes pistol grip (24) toward which closure trigger (26) is pivotally drawn by the clinician to cause clamping, or closing, of the anvil (18) toward lower jaw (16) of end effector (12). Such closing of anvil (18) is provided through an outmost closure sleeve (32), which longitudinally translates relative to handle portion (20) in response to pivoting of closure trigger (26) relative to pistol grip (24). A distal closure ring (33) of closure sleeve (32) is indirectly supported by frame (34) of implement portion (22). At articulation mechanism (11), a proximal closure tube (35) of closure sleeve (32) communicates with the distal portion (closure ring) (33). Frame (34) is flexibly attached to lower jaw (16) via articulation mechanism (11), enabling articulation in a single plane. Frame (34) also longitudinally slidingly supports a firing drive member (not shown) that extends through shaft (23) and communicates a firing motion from firing trigger (28) to firing bar (14). Firing trigger (28) is farther outboard of closure trigger (26) and is pivotally drawn by the clinician to cause the stapling and severing of clamped tissue in end effector (12), as will be described in greater detail below. Thereafter, release button (30) is depressed to release the tissue from end effector (12).

FIGS. 2-5 depict end effector (12) employing an E-beam firing bar (14) to perform a number of functions. As best seen in FIGS. 3A-3B, firing bar (14) includes a transversely oriented upper pin (38), a firing bar cap (44), a transversely oriented middle pin (46), and a distally presented cutting edge (48). Upper pin (38) is positioned and translatable within an anvil pocket (40) of anvil (18). Firing bar cap (44) slidably engages a lower surface of lower jaw (16) by having firing bar (14) extend through channel slot (45) (shown in FIG. 3B) that is formed through lower jaw (16). Middle pin (46) slidingly engages a top surface of lower jaw (16), cooperating with firing bar cap (44). Thereby, firing bar (14) affirmatively spaces end effector (12) during firing, overcoming pinching that may occur between anvil (18) and lower jaw (16) with a minimal amount of clamped tissue and overcoming staple malformation with an excessive amount of clamped tissue.

Figure 2:
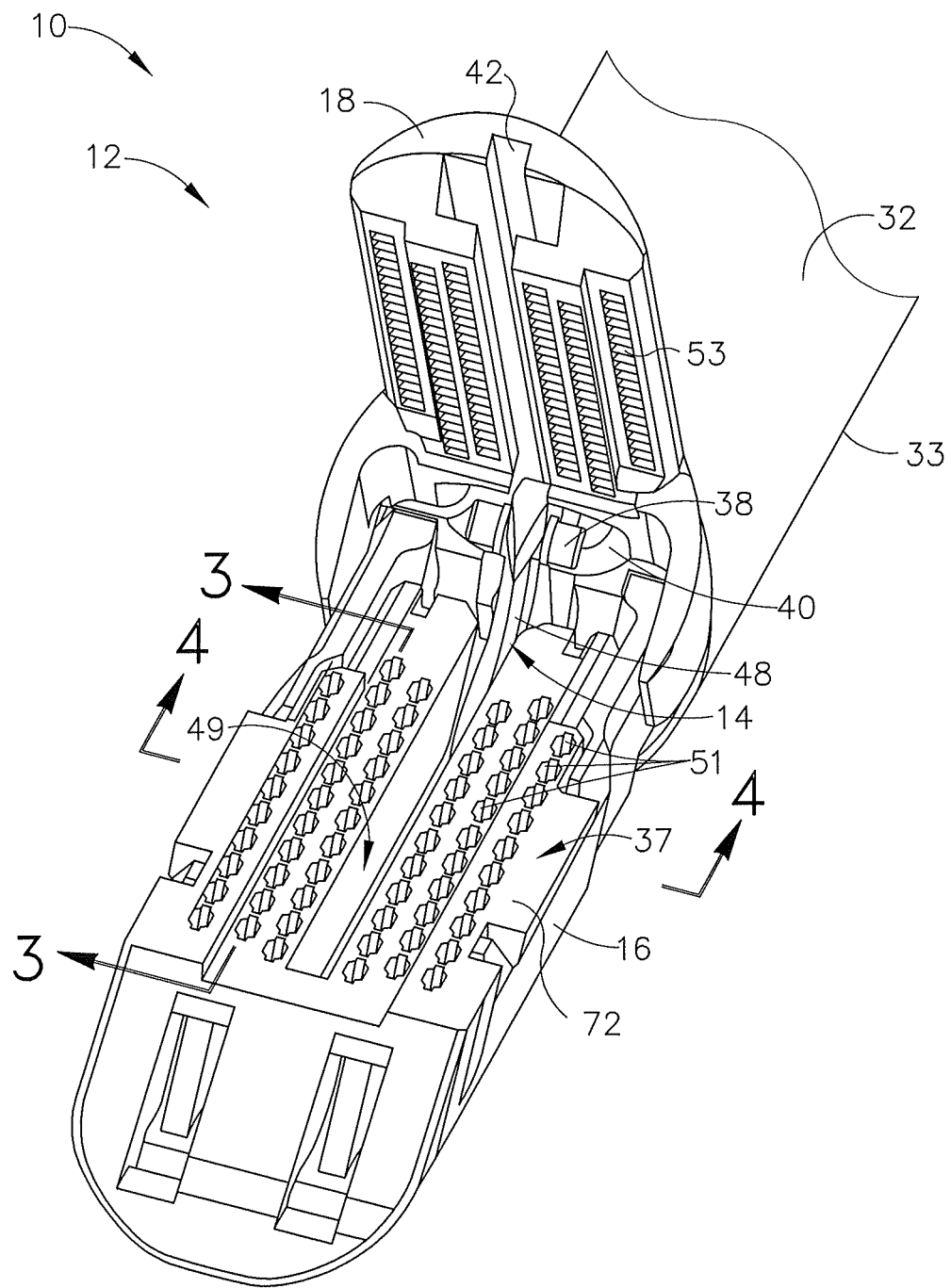
FIG. 2 depicts a perspective view of an opened end effector of the surgical instrument of FIGS. 1A-1B.
Figure 3A:
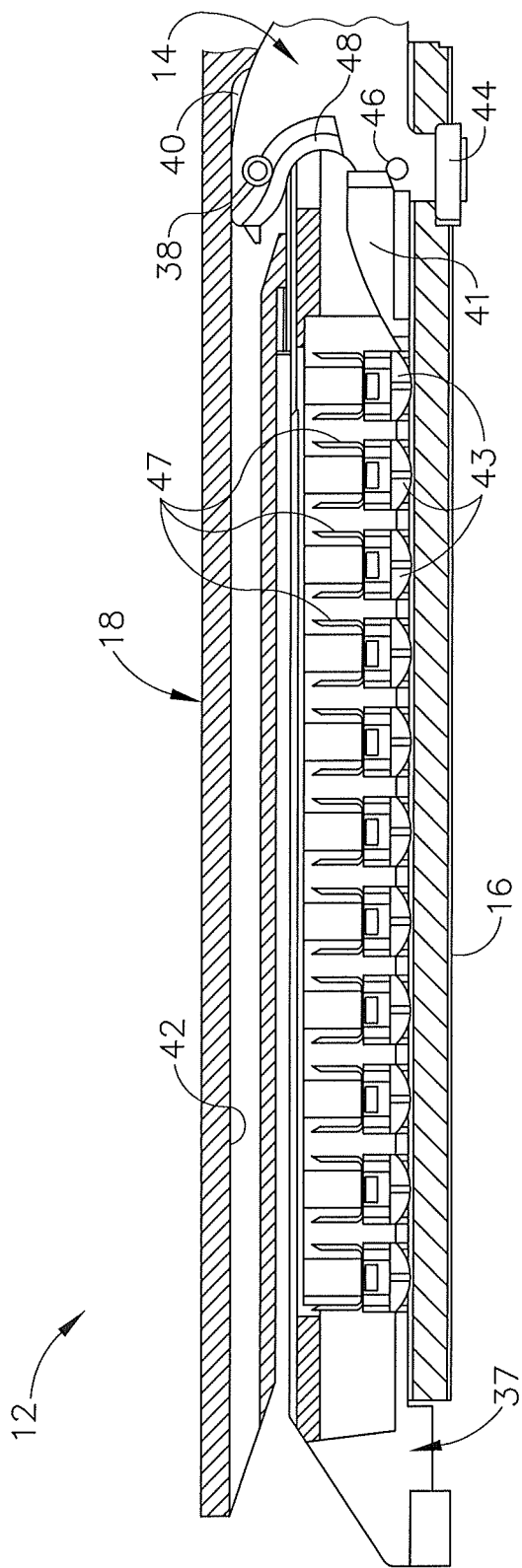
FIG. 3A depicts a side cross-sectional view of the end effector of FIG. 2, taken along line 3-3 of FIG. 2, with the firing bar in a proximal position.
Figure 3B:
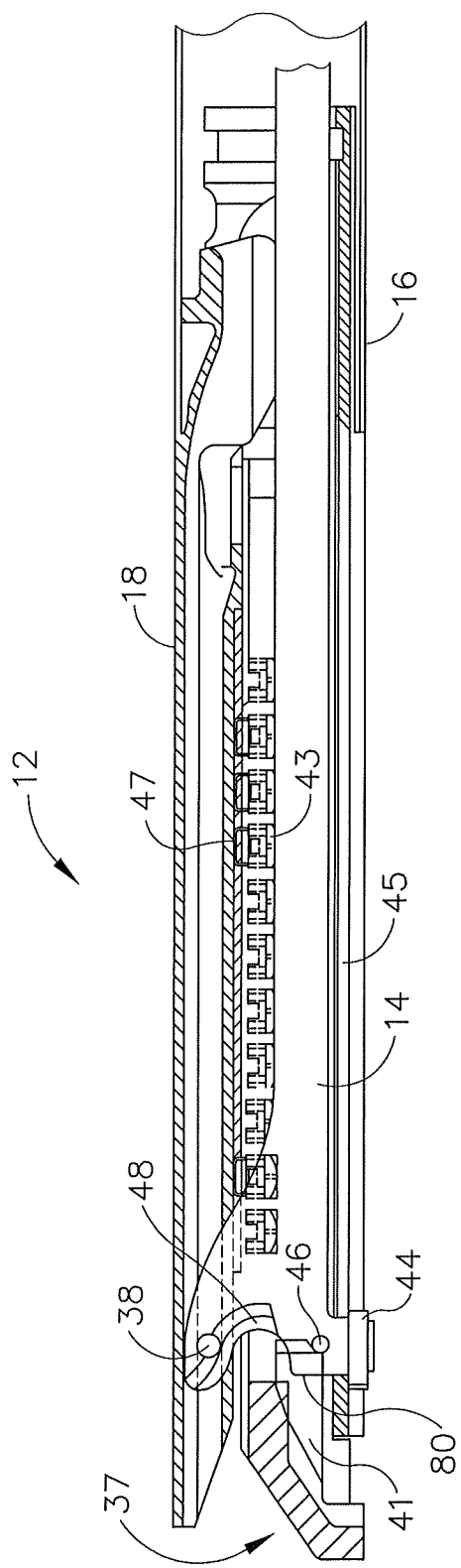
FIG. 3B depicts a side cross-sectional view of the end effector of FIG. 2, taken along line 3-3 of FIG. 2, but showing the firing bar in a distal position.
Figure 4:
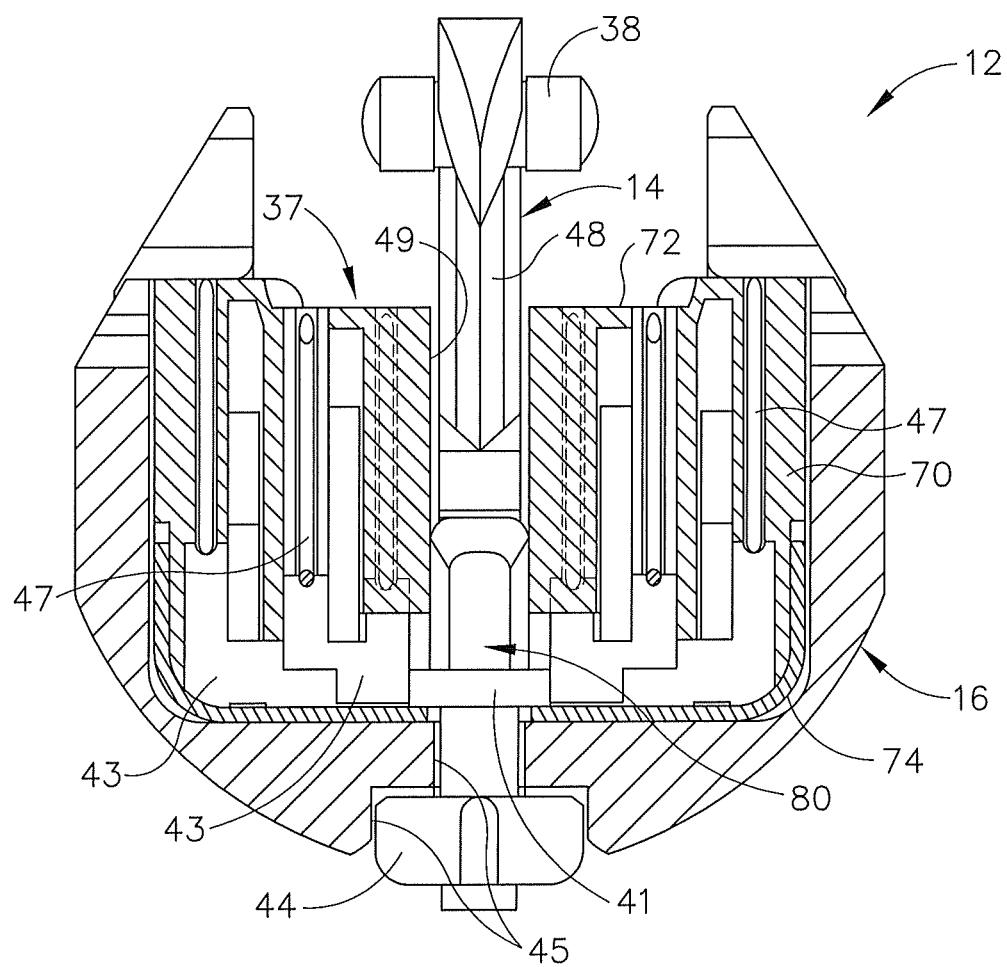
FIG. 4 depicts an end cross-sectional view of the end effector of FIG. 2, taken along line 4-4 of FIG. 2.
Figure 5:
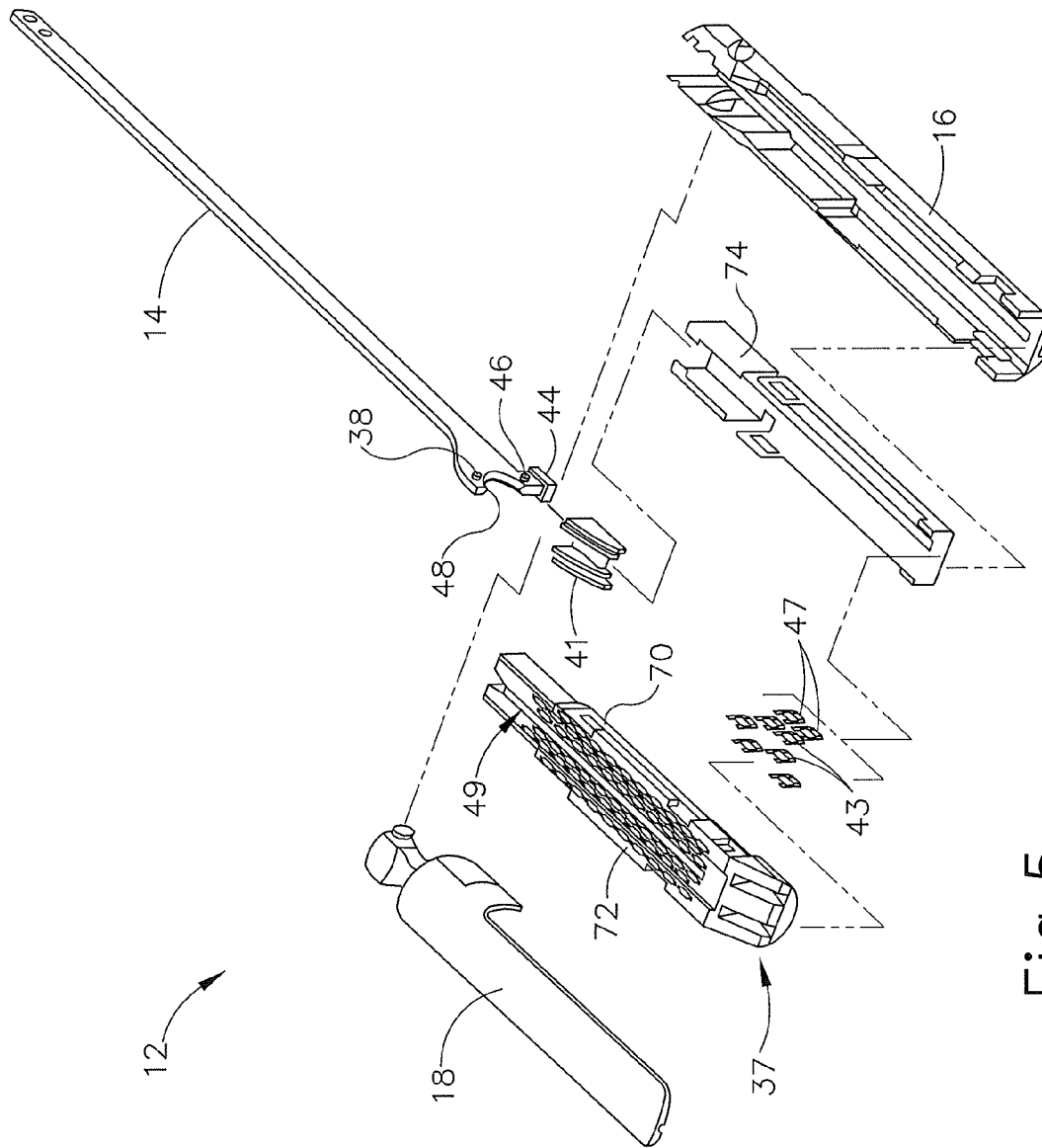
FIG. 5 depicts an exploded perspective view of the end effector of FIG. 2.

FIG. 2 shows firing bar (14) proximally positioned and anvil (18) pivoted to an open position, allowing an unspent staple cartridge (37) to be removably installed into a channel of lower jaw (16). As best seen in FIGS. 4-5, staple cartridge (37) of this example includes a cartridge body (70), which presents an upper deck (72) and is coupled with a lower cartridge tray (74). As best seen in FIG. 2, a vertical slot (49) is formed through part of staple cartridge (37). As also best seen in FIG. 2, three rows of staple apertures (51) are formed through upper deck (70) on one side of vertical slot (49), with another set of three rows of staple apertures (51) being formed through upper deck (70) on the other side of vertical slot (49). Referring back to FIGS. 3-5, a wedge sled (41) and a plurality of staple drivers (43) are captured between cartridge body (70) and tray (74), with wedge sled (41) being located proximal to staple drivers (43). Wedge sled (41) is movable longitudinally within staple cartridge (37); while staple drivers (43) are movable vertically within staple cartridge (37). Staples (47) are also positioned within cartridge body (70), above corresponding staple drivers (43). In particular, each staple (47) is driven vertically within cartridge body (70) by a staple driver (43) to drive staple (47) out through an associated staple aperture (51). As best seen in FIGS. 3A-3B and 5, wedge sled (41) presents inclined cam surfaces that urge staple drivers (43) upwardly as wedge sled (41) is driven distally through staple cartridge (37).

With end effector (12) closed as depicted in FIG. 3A, firing bar (14) is advanced in engagement with anvil (18) by having upper pin (38) enter a longitudinal anvil slot (42). A pusher block (80) is located at the distal end of firing bar (14), and is configured to engage wedge sled (41) such that wedge sled (41) is pushed distally by pusher block (80) as firing bar (14) is advanced distally through staple cartridge (37). During such firing, cutting edge (48) of firing bar (14) enters vertical slot (49) of staple cartridge (37), severing tissue clamped between staple cartridge (37) and anvil (18). As shown in FIGS. 3A-3B, middle pin (46) and pusher block (80) together actuate staple cartridge (37) by entering into a firing slot within staple cartridge (37), driving wedge sled (41) into upward camming contact with staple drivers (43) that in turn drive staples (47) out through staple apertures (51) and into forming contact with staple forming pockets (53) on the inner surface of anvil (18). FIG. 3B depicts firing bar (14) fully distally translated after completing severing and stapling tissue.

Figure 6:
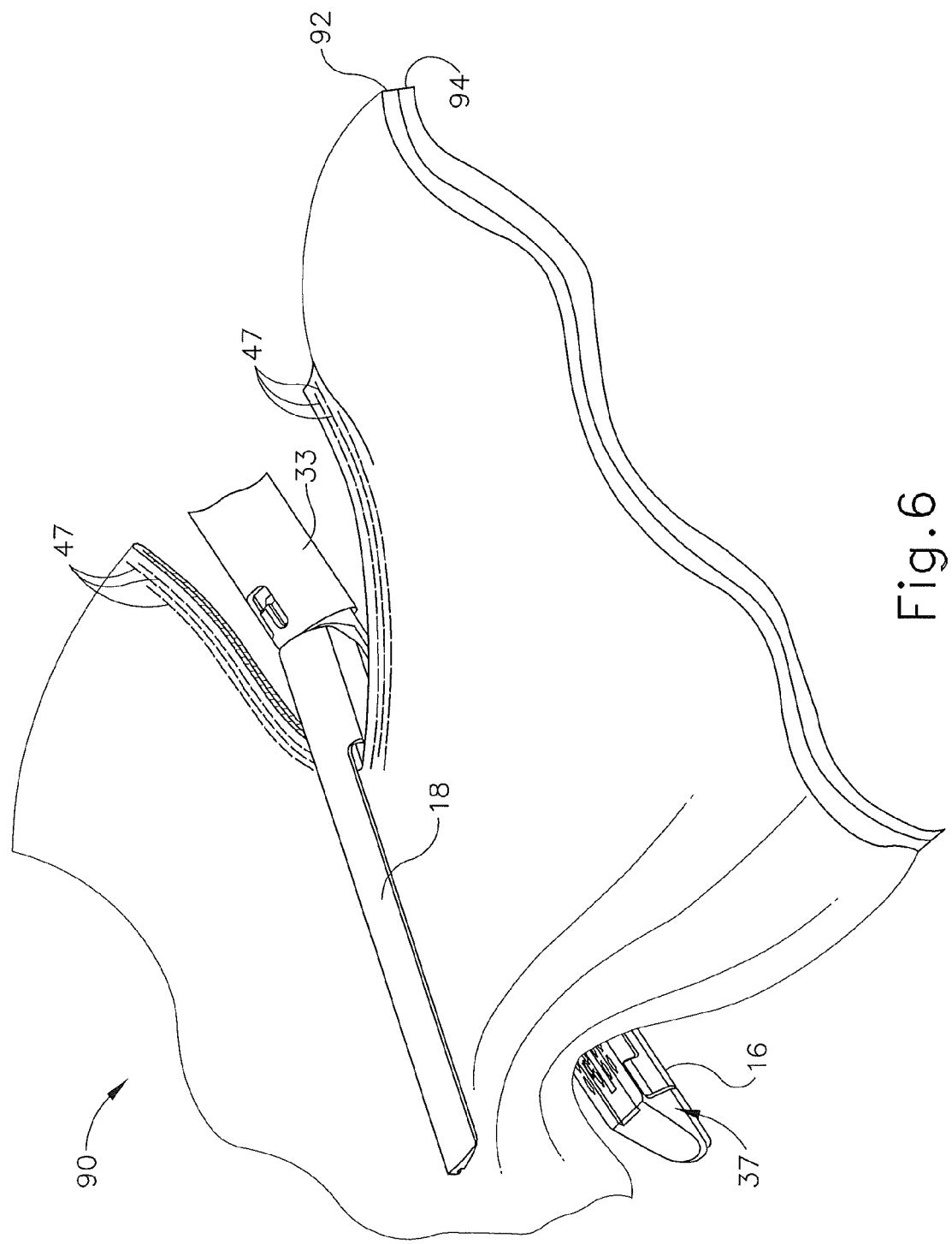
FIG. 6 depicts a perspective view of the end effector of FIG. 2, positioned at tissue and having been actuated once in the tissue.

FIG. 6 shows end effector (12) having been actuated through a single stroke through tissue (90). As shown, cutting edge (48) has cut through tissue (90), while staple drivers (43) have driven three alternating rows of staples (47) through the tissue (90) on each side of the cut line produced by cutting edge (48). Staples (47) are all oriented substantially parallel to the cut line in this example, though it should be understood that staples (47) may be positioned at any suitable orientations. In the present example, end effector (12) is withdrawn from the trocar after the first stroke is complete, spent staple cartridge (37) is replaced with a new staple cartridge, and end effector (12) is then again inserted through the trocar to reach the stapling site for further cutting and stapling. This process may be repeated until the desired amount of cuts and staples (47) have been provided. Anvil (18) may need to be closed to facilitate insertion and withdrawal through the trocar; and anvil (18) may need to be opened to facilitate replacement of staple cartridge (37).

It should be understood that cutting edge (48) may sever tissue substantially contemporaneously with staples (47) being driven through tissue during each actuation stroke. In the present example, cutting edge (48) just slightly lags behind driving of staples (47), such that a staple (47) is driven through the tissue just before cutting edge (48) passes through the same region of tissue, though it should be understood that this order may be reversed or that cutting edge (48) may be directly synchronized with adjacent staples. While FIG. 6 shows end effector (12) being actuated in two layers (92, 94) of tissue (90), it should be understood that end effector (12) may be actuated through a single layer of tissue (90) or more than two layers (92, 94) of tissue. It should also be understood that the formation and positioning of staples (47) adjacent to the cut line produced by cutting edge (48) may substantially seal the tissue at the cut line, thereby reducing or preventing bleeding and/or leaking of other bodily fluids at the cut line. Various suitable settings and procedures in which instrument (10) may be used will be apparent to those of ordinary skill in the art in view of the teachings herein.

It should be understood that instrument (10) may be configured and operable in accordance with any of the teachings of U.S. Pat. No. 4,805,823; U.S. Pat. No. 5,415,334; U.S. Pat. No. 5,465,895; U.S. Pat. No. 5,597,107; U.S. Pat. No. 5,632, 432; U.S. Pat. No. 5,673,840; U.S. Pat. No. 5,704,534; U.S. Pat. No. 5,814,055; U.S. Pat. No. 6,978,921; U.S. Pat. No. 7,000,818; U.S. Pat. No. 7,143,923; U.S. Pat. No. 7,303,108; U.S. Pat. No. 7,367,485; U.S. Pat. No. 7,380,695; U.S. Pat. No. 7,380,696; U.S. Pat. No. 7,404,508; U.S. Pat. No. 7,434, 715; and/or U.S. Pat. No. 7,721,930. As noted above, the disclosures of each of those patents are incorporated by reference herein. Additional exemplary modifications that may be provided for instrument (10) will be described in greater detail below. Various suitable ways in which the below teachings may be incorporated into instrument (10) will be apparent to those of ordinary skill in the art. Similarly, various suitable ways in which the below teachings may be combined with various teachings of the patents cited herein will be apparent to those of ordinary skill in the art. It should also be understood that the below teachings are not limited to instrument (10) or devices taught in the patents cited herein. The below teachings may be readily applied to various other kinds of instruments, including instruments that would not be classified as surgical staplers. Various other suitable devices and settings in which the below teachings may be applied will be apparent to those of ordinary skill in the art in view of the teachings herein.

II. Exemplary Filled Staples

Figure 7:
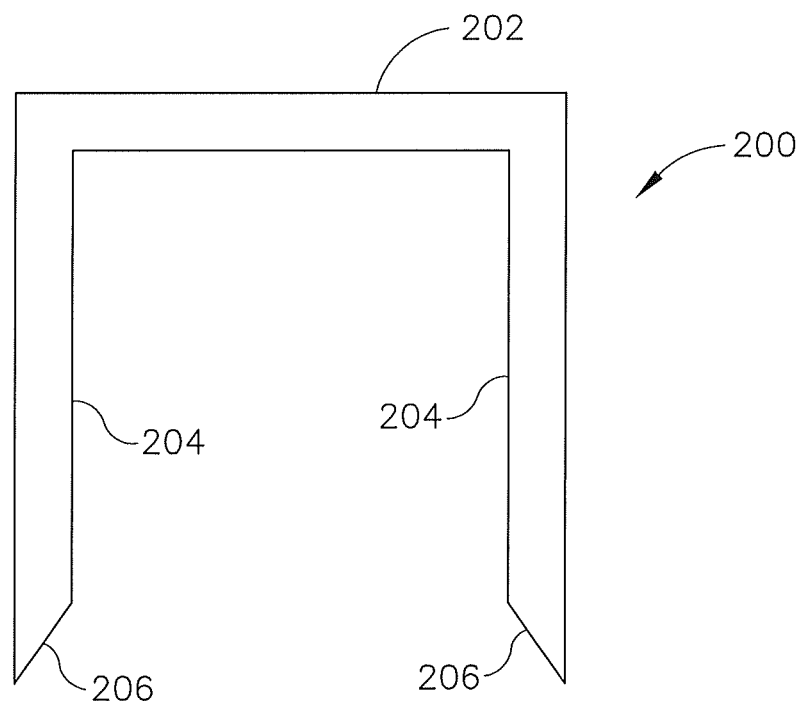
FIG. 7 depicts a front elevational view of an exemplary version of a staple.

In the exemplary version shown in FIGS. 1-6, it will be appreciated that staples (47) may comprise surgical staples as depicted, for example, in FIGS. 3A-4. For further illustration, FIG. 7 shows an enlarged view of a staple (200) for use with surgical severing and stapling instrument (10) as shown in FIGS. 1-6. Staple (200) comprises a crown (202), legs (204), and teeth (206). In some exemplary versions, staple (200) may be constructed from a wire having a circular or substantially round cross-section. In other versions, staple (200) may be constructed from a wire or strip of material having a rectangular or a substantially flat cross-section. It will be appreciated that other variations of shapes and sizes of staple (200) may be used as would be apparent to one of ordinary skill in the art in view of the teachings herein.

Figure 8:
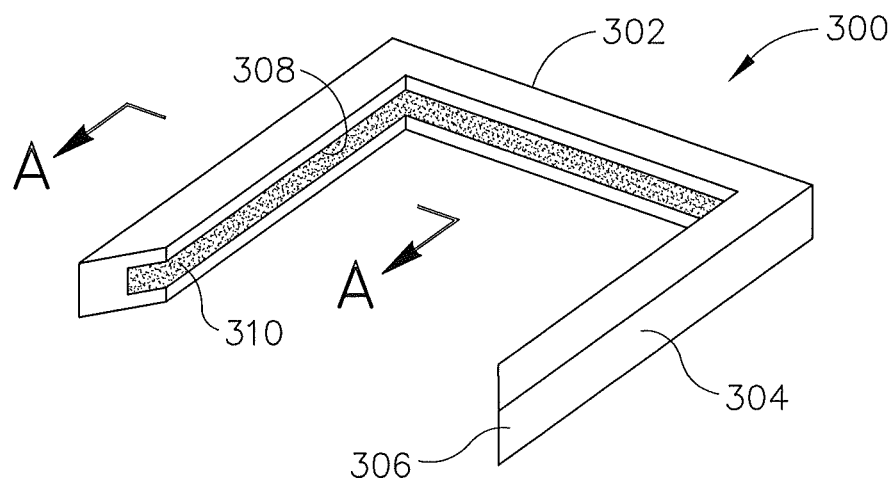
FIG. 8 depicts a perspective view of an alternative exemplary version of a staple.

It will be appreciated that it may be desirable to have staple (200) aid or facilitate coagulation of blood or other fluids at the surgical site. In some other merely exemplary versions, it may be desirable to have staple (200) aid in the healing of the surgical site by providing a therapeutic agent to the surgical site. For example, FIG. 8 shows an exemplary staple (300) for use with surgical severing and stapling instrument (10). Staple (300) comprises a crown (302), legs (304), and teeth (306). Staple (300) further comprises an inner channel (308). As shown in the exemplary version, inner channel (308) extends around the entire inner portion of staple (300) from teeth (306), through legs (304), and through crown (302). In some exemplary versions, inner channel (308) may extend only around a portion of staple (300). For example, inner channel (308) may only extend through crown (302). In other exemplary versions, inner channel (308) may only extend through legs (304). Other suitable lengths for inner channel (308) may be used as would be apparent to one of ordinary skill in the art in view of the teachings herein. In the exemplary version, teeth (306) have a pointed shape, but any suitable shape for teeth (306) may be used as would be apparent to one of ordinary skill in the art in view of the teachings herein. For example, teeth (306) may comprise a rectangular or otherwise blunt surface.

In the illustrated version, inner channel (308) holds an agent (310). Agent (310) in the exemplary version comprises a powder mixture of thrombin and fibrin operable to aid in coagulation of the area surrounding staple (300) once staple (300) is inserted at the surgical site. While the exemplary version comprises thrombin and fibrin, it will be appreciated that any suitable coagulant may be used as would be apparent to one of ordinary skill in the art in view of the teachings herein. Furthermore, in some versions, other therapeutic agents in addition to a coagulant may be used. For example, agent (310) may comprise a material operable to aid in healing of the surgical site. Merely exemplary therapeutic agents may include antibiotics, hemostatic agents, adhesives, sealants, oncological drugs, radioactive materials, and/or any other suitable agents as would be apparent to one of ordinary skill in the art in view of the teachings herein. In some exemplary versions, agent (310) may comprise a mixture of a healing agent as well as a coagulant or any other suitable materials as would be apparent to one of ordinary skill in the art in view of the teachings herein. In some other exemplary versions, it will be appreciated that agent (310) may be placed in inner channel (308) or staple (300) while a separate therapeutic agent, such as any of those discussed herein may be applied to the outer surface of staple (300) rather than only being applied to inner channel (308).

Figure 9:
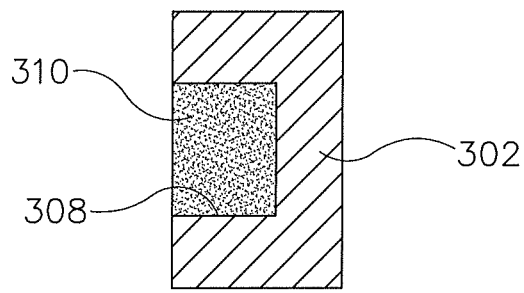
FIG. 9 depicts a cross sectional view along line A-A of the staple shown in FIG. 8.

In the illustrated version, agent (310) comprises a powder mixture as stated above. The powder mixture of agent (310) is operable to stay sufficiently packed within inner channel (308) such that agent (310) does not fall out of inner channel (308). Once staple (300) is inserted into the surgical site, the powder mixture may be activated by mixing with the blood and/or other fluids at the surgical site, thereby initiating the coagulation process. As agent (310) near the exposed portion of inner channel comes into contact with bodily fluid, more and more powder material in inner channel (308) absorbs fluid from the surgical site. Powder material combined with fluid forms a thicker fluid, where a portion of the thicker fluid flows out of inner channel (308). As a result, agent (310) is able to spread to other portions of the surgical site other than those directly adjacent to staple (300). It will be appreciated that coagulation of blood and other fluids of the surgical site as a result of coming in contact with agent (310) may result in additional stability of staples (300) inserted into surgical site. It will further be appreciated that once staple (300) is inserted into the surgical site, the operation of surgical severing and stapling instrument (10) results in legs (304) of staple (300) folding inward. As a result, this deformation of a part of staple (300) may aid staple (300) in urging agent (310) out of staple (300). While the present exemplary agent (310) has a powder state, agent (310) may be of a freeze dried form where agent (310) has been injected into inner channel (308), thereafter being freeze dried once agent (310) is positioned within inner channel (308). In other exemplary versions, any suitable fluid state for agent (310) may be used as would be apparent to one of ordinary skill in the art in view of the teachings herein. FIG. 9 shows a cross section of staple (300) having a generally rectangular cross section showing agent (310) packed into inner channel (308) prior to use.

In some versions, agent (310) may comprise a gel or other liquid agent (310) that remains generally within inner channel (308) until staple (300) is inserted at surgical site. For example, it will be appreciated that a liquid or gel used as agent (310) may stay within inner channel (308) due to the liquid tension being operable to retain agent (310) within inner channel (308). Once staple (300) is inserted into the surgical site, agent (310) may come into contact with fluids and/or tissue which essentially breaks the surface tension of agent (310), thereby allowing agent (310) to interact with the surgical site.

It should also be understood that rather than having an exposed inner channel (308) extending around staple (300), staple (300) may define a hollow cylindrical cross-section such that inner channel (308) may only be exposed to the surgical site at teeth (306). Such a configuration for staple (300) may be constructed by forming inner channel (308) within a long wire, which may be subsequently cut and bent to form staple (300). Other suitable methods of forming staple (300) may be used as would be apparent to one of ordinary skill in the art in view of the teachings herein. As a result, agent (310) contained within inner channel (308) is released to the surgical site through teeth (306) providing for a slower release of agent (310). Any suitable configuration for inner channel (308) may be used as would be apparent to one of ordinary skill in the art in view of the teachings herein. It will further be appreciated that inner channel (308) within staple (300) may be operable to act as a capillary such that once inserted into a surgical site, staple (300) may have agent (310) drawn out from staple (300).

Figure 10:
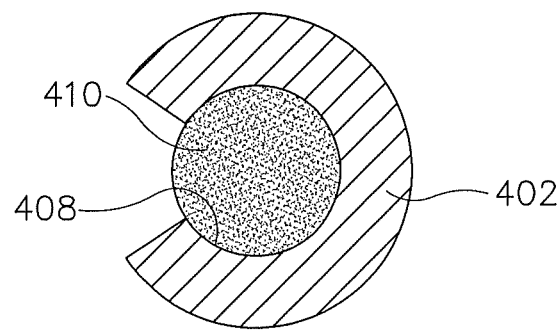
FIG. 10 depicts a cross sectional view of yet another alternative exemplary version of a staple having a c-shaped cross section.

In FIG. 10, an exemplary version of staple (400) has a c-shaped cross section rather than a rectangular cross section. In some exemplary versions, staple (400) may be formed using an elongate wire. The elongate wire may have a channel formed therein along the length of staple (400), which forms inner channel (408). In some exemplary versions, staple (400) may be formed using a rolled piece of material that may be filled with agent (410). For example, the material for forming staple (400) may be laid out in a flattened manner. Then a suitable amount of agent (410) may be placed in the material, wherein the material may then be rolled. A portion of material may be cut and then bent to form staple (400). As a result, the process may yield a circular cross section as shown in FIG. 10. However, a similar process may be used to form staples (400) having any suitable cross section as would be apparent to one of ordinary skill in the art in view of the teachings herein. Furthermore, any other suitable method for forming staple (400) may be used as would be apparent to one of ordinary skill in the art in view of the teachings herein.

Figure 11:
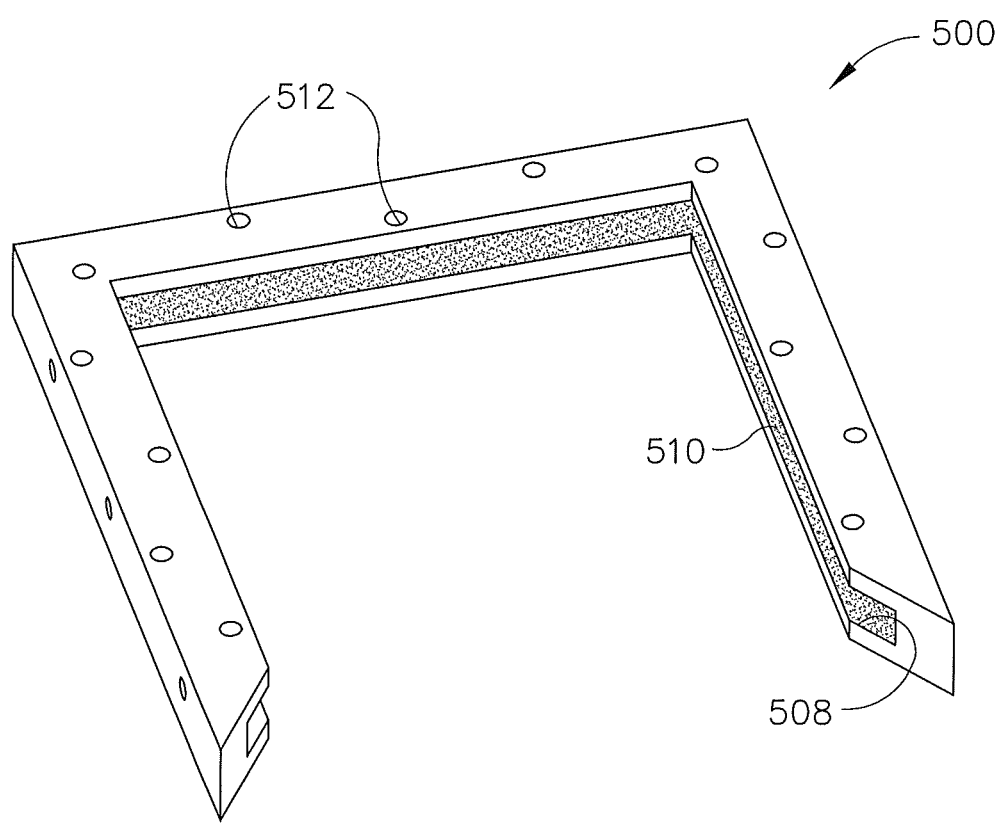
FIG. 11 depicts a front, perspective view of yet another alternative exemplary version of a staple having a plurality of holes.

FIG. 11 shows an alternative exemplary version of a staple (500) having an inner channel (508) containing an agent (510). In the exemplary version, staple (500) further comprises a plurality of holes (512) spread across the surface of staple (500). Holes (512) may be spread evenly as shown in the present example, or in other exemplary versions, holes (512) may be concentrated more highly in one particular area than another. Furthermore, while the present example shows holes (512) having a generally circular shape, it will be appreciated that any size or shape for holes (512) may be used as would be apparent to one of ordinary skill in the art in view of the teachings herein. It will be appreciated that once staple (500) is applied to a surgical site, holes (512) may facilitate the release of agent (510) to the surgical site by agent (510) being released to the site through holes (512) or by exiting directly from inner channel (508). It will further be appreciated that holes (512) may be operable to provide support for tissue growth once staple (500) is inserted into a surgical site. It will be understood that other suitable functionalities may result and are contemplated as a result of holes (512) in staple (500).

It will be understood that staples (300, 400, 500) as described herein may be configured such that they are loadable and otherwise compatible with a conventional staple cartridge (37) without having to provide special accommodations for staples (300, 400, 500). Furthermore, once agent (310, 410, 510) is injected into staple (300, 400, 500), staples (300, 400, 500) are still sized to fit conventional staple cartridges (37). It will be understood, however, that staples (300, 400, 500) may be constructed to be any suitable size and configuration as would be apparent to one of ordinary skill in the art in view of the teachings herein, even if such sizes or configurations would exceed the sizes of conventional staple cartridges (37).

It should be understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

Versions of the devices described above may have application in conventional medical treatments and procedures conducted by a medical professional, as well as application in robotic-assisted medical treatments and procedures.

Versions of described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or Tyvek bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various versions in the present disclosure, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, versions, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus, comprising:
   (a) a surgical instrument comprising a proximal end and a distal end, wherein the proximal end of the surgical instrument comprises a handle, wherein the distal end of the surgical instrument comprises a cutter and a stapler;
   (b) a staple in communication with the stapler, wherein the staple comprises a hollowed out portion, wherein the hollowed out portion extends the entire length of the staple, wherein the stapler of the surgical instrument is configured to deliver the staple to a surgical site; and
   (c) an agent positioned in the hollowed out portion of the staple, wherein the hollowed out portion is further configured to release at least a portion of the agent.

2. The apparatus of claim 1, wherein the agent comprises fibrin and thrombin.

3. The apparatus of claim 1, wherein the agent comprises a powder form.

4. The apparatus of claim 1, wherein the staple has a rectangular cross section.

5. The apparatus of claim 1, wherein the staple has a c-shaped cross section.

6. The apparatus of claim 1, wherein the agent comprises a gel form.

7. The apparatus of claim 1, wherein the agent comprises a freeze dried liquid.

8. The apparatus of claim 1, wherein the staple further comprises at least one aperture connecting the hollowed out portion and the outer surface of the staple.

9. The apparatus of claim 1, further comprising an adjunct therapeutic agent, wherein the adjunct therapeutic agent is contained within the hollowed out portion mixed with the agent.

10. The apparatus of claim 1, wherein the staple comprises a crown, a leg portion, and a pair of teeth, wherein each tooth has a blunt shape.

11. The apparatus of claim 1, wherein the staple comprises a crown, a leg portion, and a pair of teeth, wherein each tooth has a pointed shape.

12. The apparatus of claim 1, wherein the staple comprises a therapeutic coating applied to the outer surface of the staple.

13. The apparatus of claim 1, wherein the agent comprises a freeze dried agent.

14. The apparatus of claim 1, wherein the agent is configured to activate when combined with a liquid, wherein the agent is configured to aid in coagulation once the agent is activated.

15. The apparatus of claim 1, wherein the staple is operable to be deformed as the staple is delivered to a surgical site, wherein the deformation of the staple urges out at least a portion of the agent.

16. An apparatus comprising:
   (a) a surgical cutter and stapler, wherein the surgical cutter and stapler are configured to sever a portion of tissue, wherein the surgical cutter and stapler are further configured to staple the severed portion of surgical tissue; and
   (b) a staple in communication with the surgical cutter and stapler, wherein the staple is configured to be delivered to a surgical site, wherein the staple comprises a hollowed out portion extending the entire length of the staple, wherein the staple further comprises an agent, wherein the agent is positioned in the hollowed out portion of the staple, wherein the agent is configured to coagulate a fluid, wherein the agent is configured to be activatable to coagulate a fluid upon contact with a fluid material.

17. The apparatus of claim 16, wherein the agent comprises a mixture of fibrin and thrombin.

18. The apparatus of claim 16, wherein the agent comprises a freeze dried material.

19. The apparatus of claim 16, wherein the staple defines a c-shaped cross section.

20. An apparatus, comprising:
   (a) a surgical instrument comprising a proximal end and a distal end, wherein the distal end of the surgical instrument comprises a stapler;
   (b) a staple in communication with the stapler, wherein the staple comprises a hollowed out portion, wherein the hollowed out portion extends the entire length of the staple, wherein the stapler of the surgical instrument is configured to deliver the staple to a surgical site; and
   (c) an agent positioned in the hollowed out portion of the staple, wherein the hollowed out portion of the staple is further configured to release at least a portion of the agent.

* * * * *